(12) United States Patent
Wolleschensky

(10) Patent No.: US 7,872,799 B2
(45) Date of Patent: Jan. 18, 2011

(54) DEVICE FOR CONTROLLING LIGHT RADIATION

(75) Inventor: Ralf Wolleschensky, Apolda (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 0 days.

(21) Appl. No.: 12/318,287

(22) Filed: Dec. 23, 2008

(65) Prior Publication Data

US 2009/0257107 A1    Oct. 15, 2009

Related U.S. Application Data

(63) Continuation of application No. 11/998,418, filed on Nov. 30, 2007, now abandoned, which is a continuation of application No. 11/416,392, filed on May 3, 2006.

(30) Foreign Application Priority Data

May 3, 2005    (DE)    ........................ 10 2005 020 545

(51) Int. Cl.
*G02B 21/06*    (2006.01)
(52) U.S. Cl. ........................ 359/386; 359/495; 359/388
(58) Field of Classification Search ................ 359/386, 359/388, 494, 495
See application file for complete search history.

(56) References Cited

U.S. PATENT DOCUMENTS

| 6,525,812 B1 | 2/2003 | Hartmann et al. |
| 2001/0046050 A1 | 11/2001 | Hoyt |
| 2004/0159797 A1 * | 8/2004 | Wolleschensky ......... 250/458.1 |

FOREIGN PATENT DOCUMENTS

| DE | 10241472 A1 | 3/2004 |
| DE | 10247247 A1 | 4/2004 |
| EP | 1396739 | * 3/2004 |
| GB | 2076994 A | 12/1981 |

OTHER PUBLICATIONS

A.M. Weiner: "Femtosecond pulse shaping using spatial light modulators," American Institute of Physics; Review of Scientific Instruments, vol. 71, No. 5, May 2000.
M.A. Dugan, et al: "High-resolution acousto-optic shping of unamplified and amplified femtosecond laser pulses," Optical Society of America; J.Opt.Soc. Am. B, vol. 14, No. 9, Sep. 1997.
C.W. Hillegas, et al: "Femtosecond laser pulse shaping by use of microsecond radio-frequency pulses," Optical Society of America; Optics Letters, vol. 19, No. 10, May 15, 1994.
Patrick Nuernberger, et al: "Femtosecond quantum control of molecular dynamics in the condensed phase," The Owner Societies; Physical Chemistry Chemical Physics, Mar. 13, 2007.
F. Verluise, et al: "Amplitude and phase control of ultrashort pulseds by use of an acousto-optic programmable dispersive filter: pulse compression and shaping," Optical Society of America; Optics Letters, vol. 25, No. 8, Apr. 15, 2000.

* cited by examiner

*Primary Examiner*—Joshua L Pritchett
(74) *Attorney, Agent, or Firm*—Jacobson Holman PLLC

(57) ABSTRACT

Device for controlling light radiation, which is excited in a specimen and/or which is backscattered and/or reflected and which contains one or more wavelengths, at a plurality of light outlets, wherein a separation of the light radiation into differently polarized components is carried out; and the components of the excitation radiation and/or detection radiation are affected in their polarization by means of a preferably birefringent, preferably acousto-optic or electro-optic medium, which changes the ordinary and extraordinary refractive index.

10 Claims, 13 Drawing Sheets

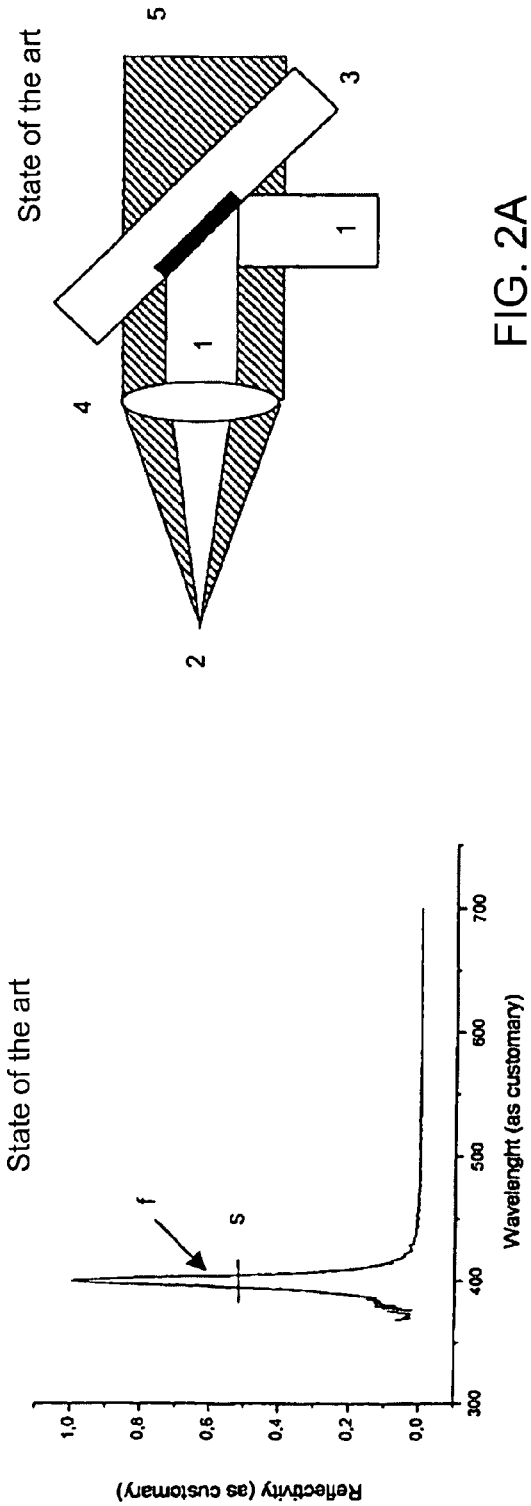
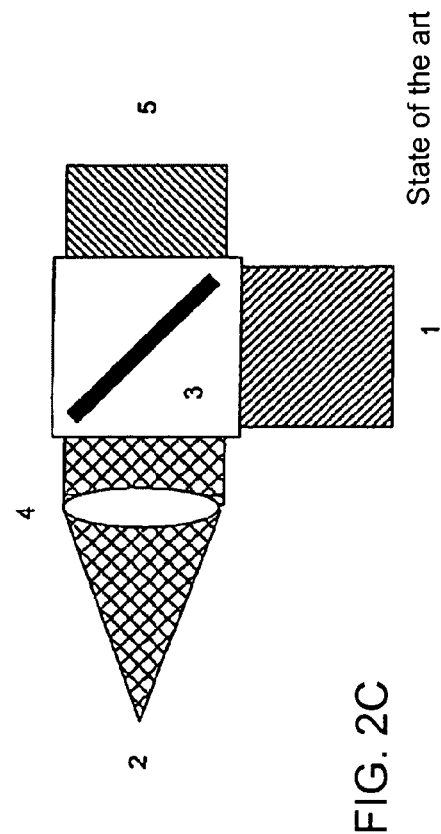
FIG. 2A
FIG. 2B
FIG. 2C

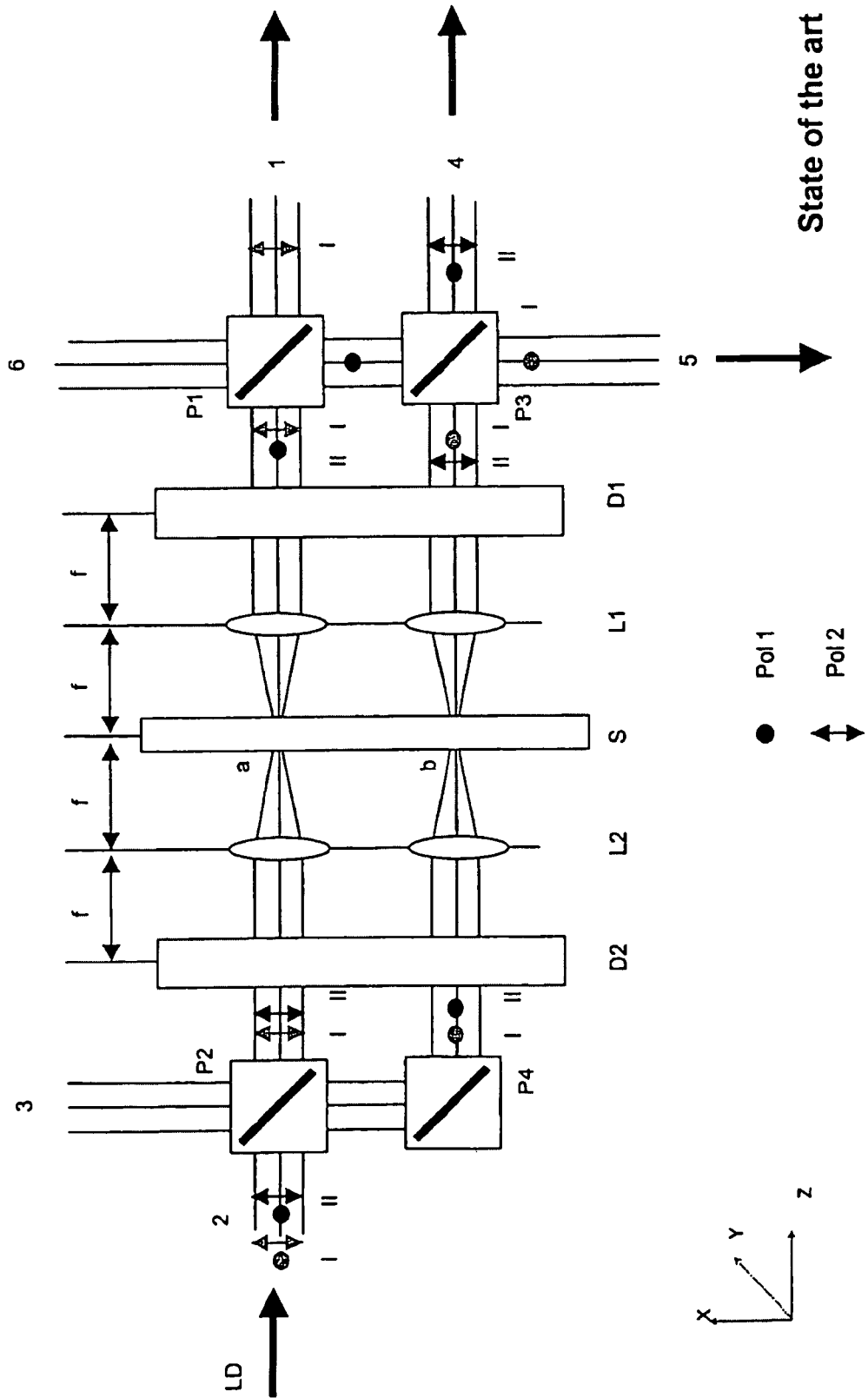
FIG. 4  State of the art

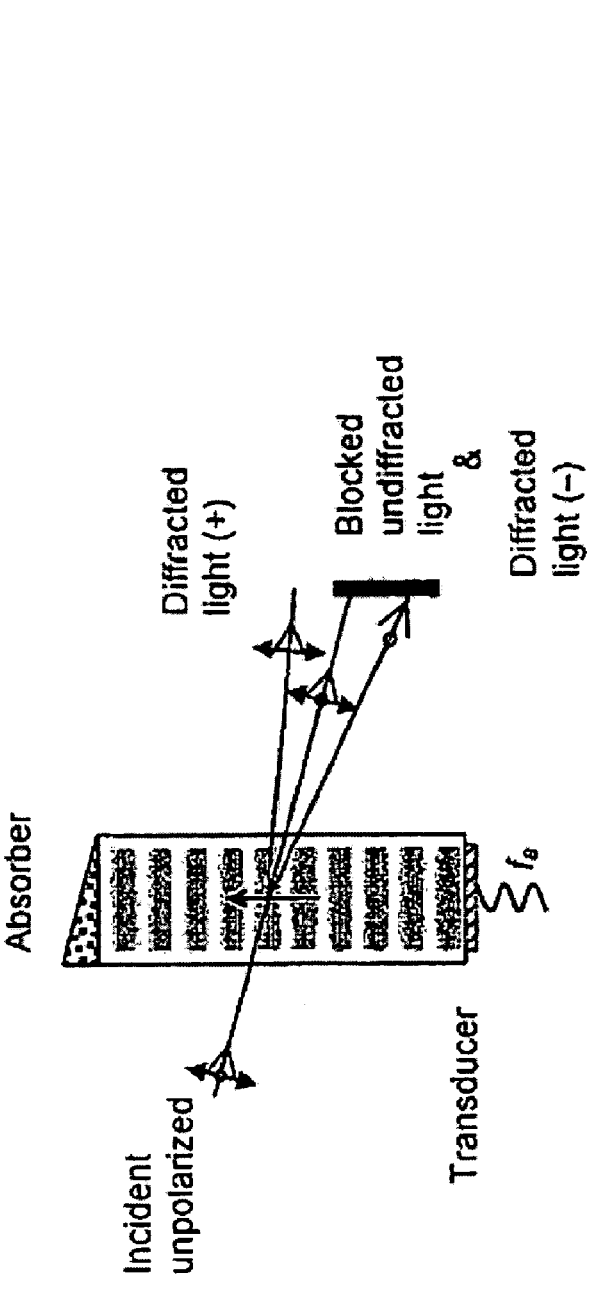
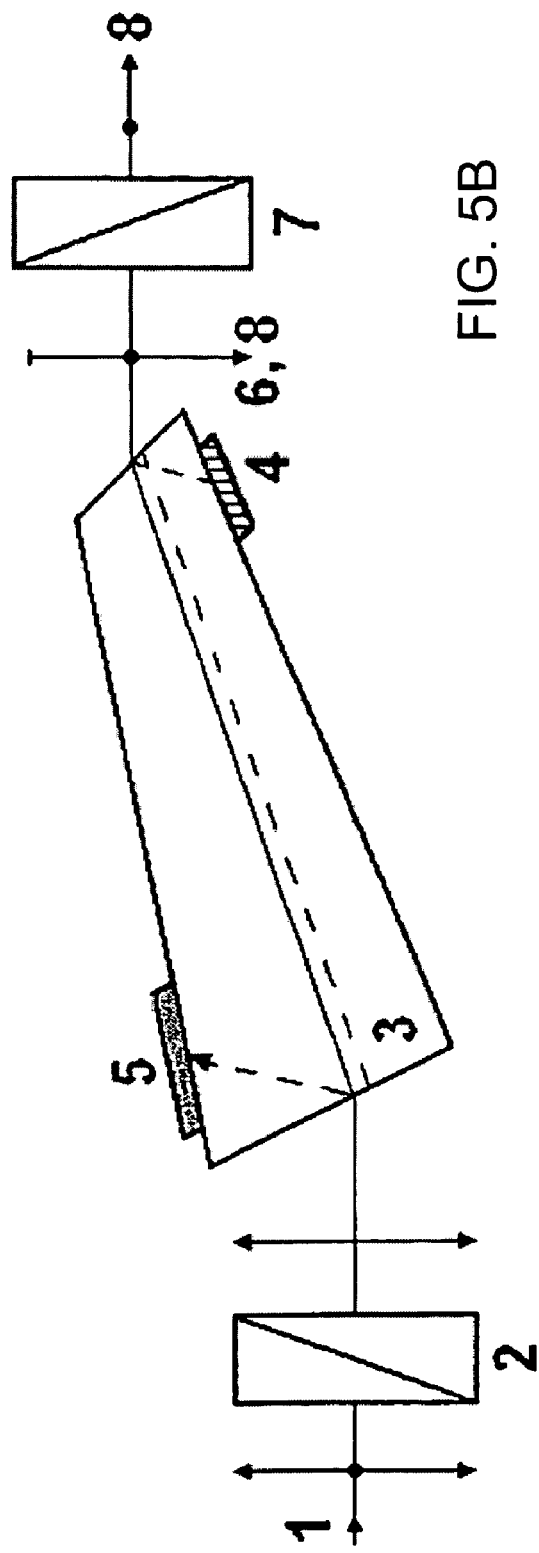
FIG. 5A
FIG. 5B

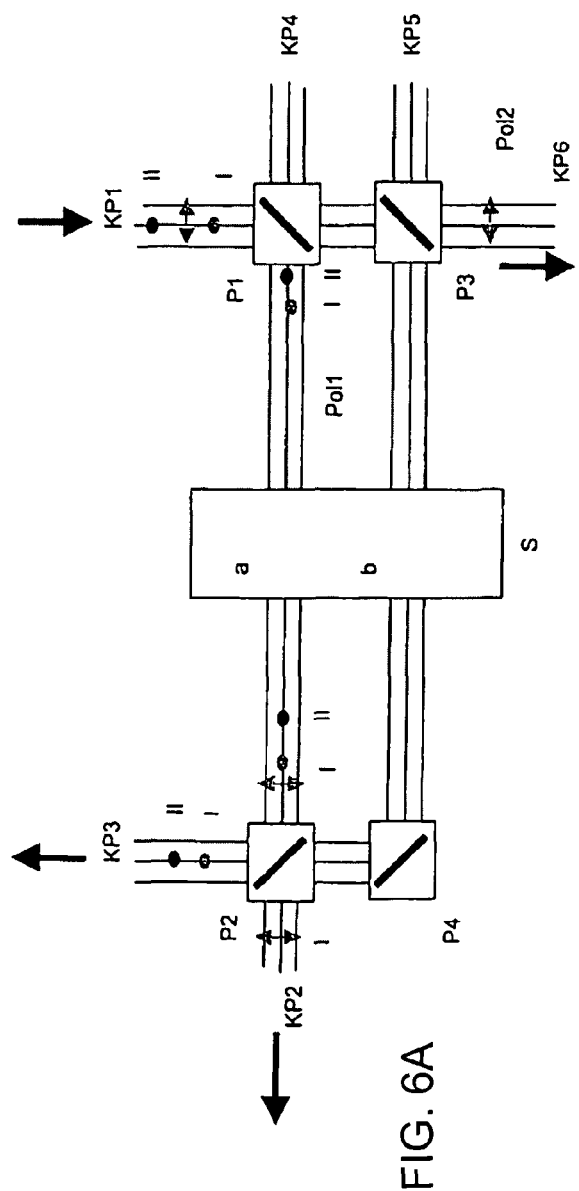
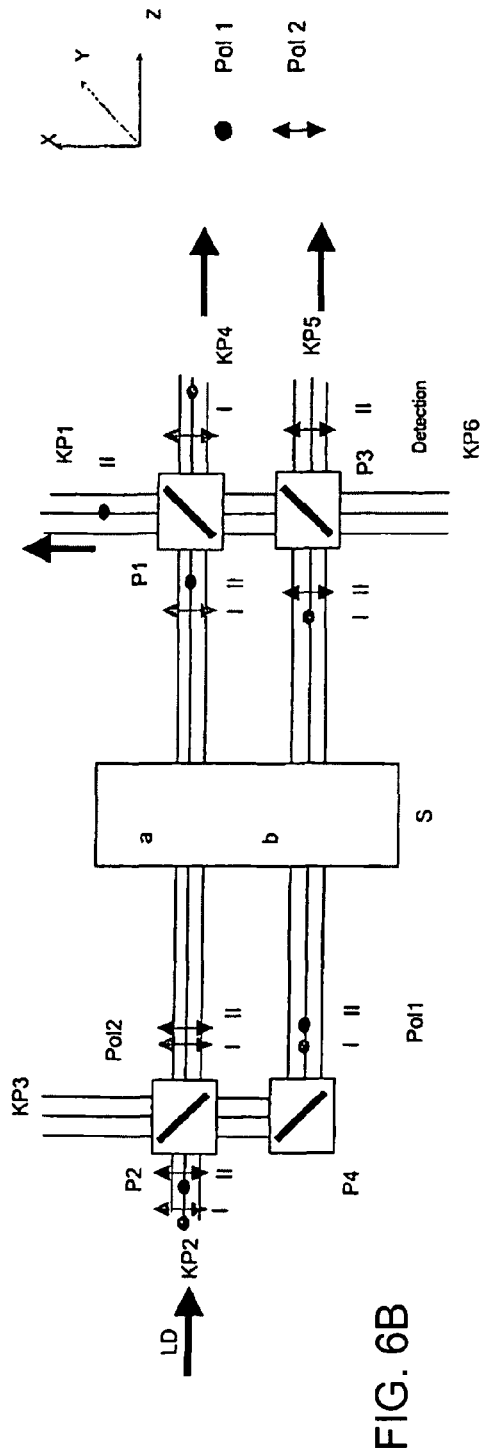
FIG. 6A
FIG. 6B

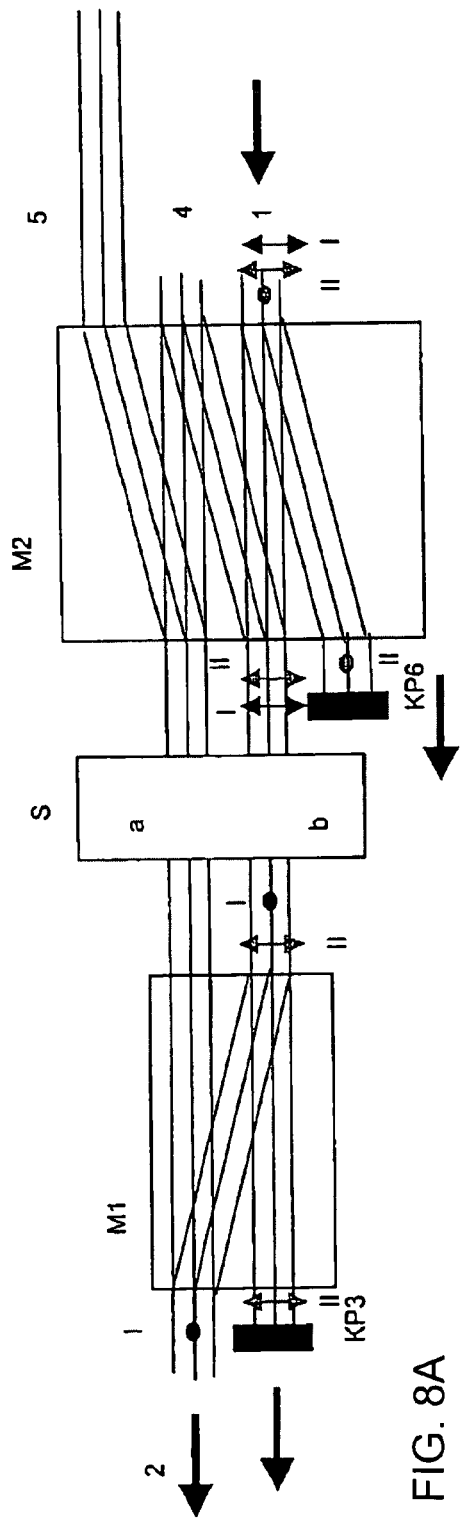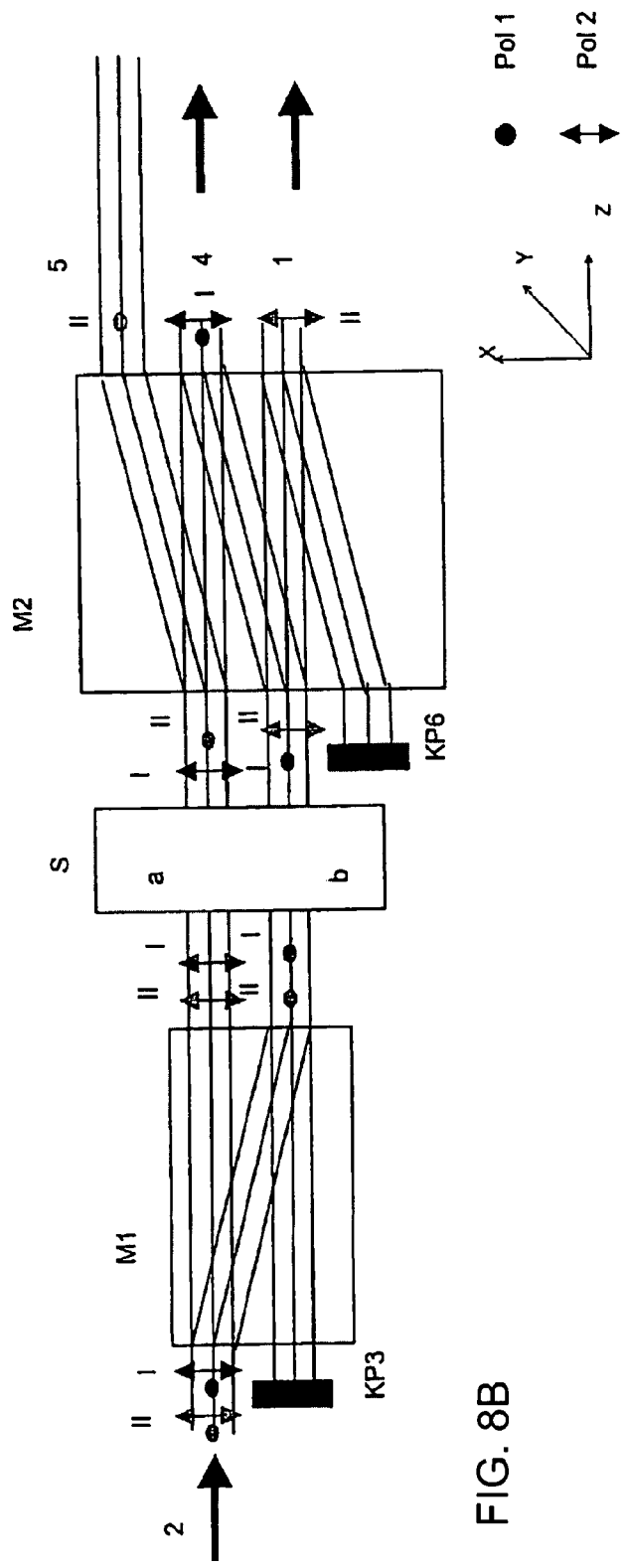
FIG. 8A
FIG. 8B

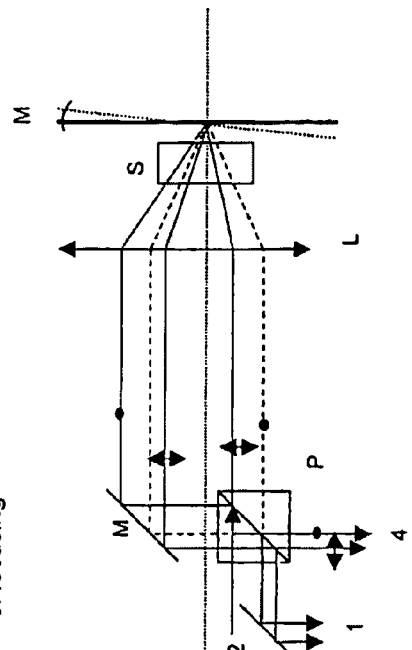
FIG. 9A
Backside of S has a mirror
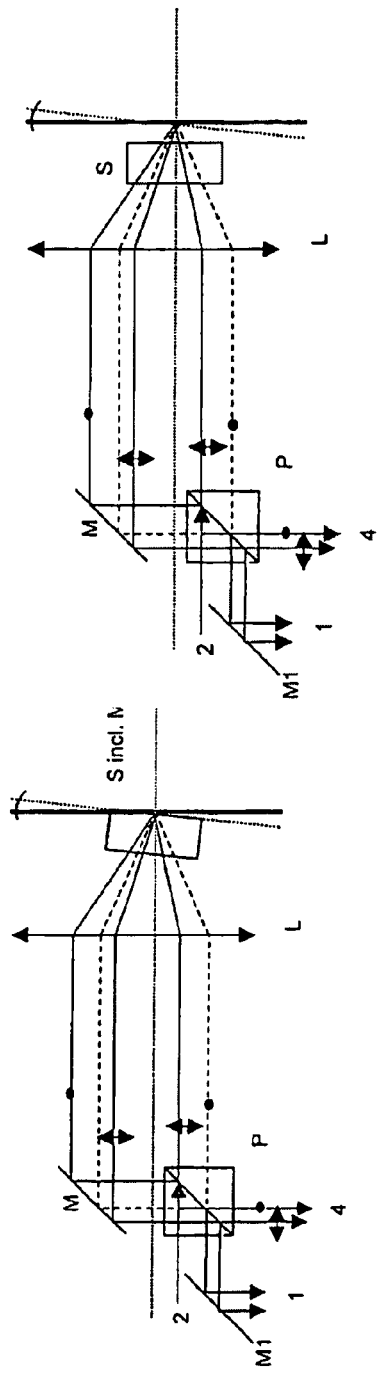
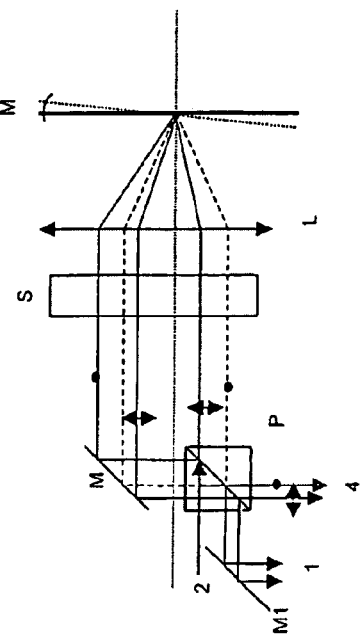
FIG. 9B
S is transparent and has a large diameter
FIG. 9C
S is transparent and has a small diameter, so that all 4 beams pass through by means of focusing

DEVICE FOR CONTROLLING LIGHT RADIATION

CROSS-REFERENCE TO RELATED APPLICATIONS

The present patent application is a continuation of application Ser. No. 11/998,418 filed Nov. 30, 2007 now abandoned, which is a continuation of application Ser. No. 11/416,392, filed May 3, 2006, both of which are incorporated herein by reference in their entireties.

BACKGROUND OF THE INVENTION

1. Field of the Invention

The invention relates to a method and arrangements in microscopy, in particular fluorescence microscopy, laser scanning microscopy, fluorescence correlation spectroscopy and near-field scanning microscopy, for examining predominantly biological specimens, preparations and related components. This includes methods for screening active ingredients based on fluorescence detection (high throughput screening) as well as methods of flow cytometry. Therefore, simultaneous examinations of specimens with multiple fluorophores in real time by means of simultaneous illumination of the specimen at multiple sampling points are possible with overlapping fluorescence spectra even in three dimensional structures of thick specimens.

2. Related Art

A typical field of application of light microscopy for examining biological preparations is fluorescence microscopy (literature: Pawley. *Handbook of Biological Confocal Microscopy*. Plenum Press, 1995). In this case, specific dyes are used for specific labeling of cell parts.

The beamed-in photons having a determined energy excite the dyed molecules, through the absorption of a photon, from the original state into an excited state. This excitation is usually referred to as single photon absorption. The dyed molecules that are excited in this way can return to the original state in various ways. In fluorescence microscopy the most important way is has a longer wavelength. The Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes that bind in a specific manner (multiple fluorescence). Special dichroic beam splitters are used in turn to distinguish the fluorescence signals, emitted by the individual dyes.

In addition to excitation of dyed molecules with a high-energy photon (single photon absorption), excitation with a plurality of low-energy photons is also possible. The sum of energies of the single photons is equal to approximately a multiple of the high-energy photon. This type of excitation of dyes is known as multiphoton absorption (literature: Corle, Kino. *Confocal Scanning Optical Microscopy and Related Imaging Systems*. Academic Press, 1996). However, the dye emission is not influenced by this type of excitation. That is, the emission spectrum undergoes a negative Stokes shift in multiphoton absorption; thus, it has a shorter wavelength compared to the excitation radiation. The separation of the excitation radiation from the emission radiation is carried out in the same way as in single photon absorption.

The prior art shall be explained below in detail by way of example with reference to a confocal laser scanning microscope (LSM) (FIG. 1). An LSM is essentially composed of four modules: light source, scan module, detection unit and microscope. These modules are described below in detail. In addition, reference is made to U.S. Pat. No. 6,167,173 A.

Lasers with different wavelengths are used in an LSM for specific excitation of different dyes in a preparation. The choice of excitation wavelengths is governed by the absorption characteristics of the dyes to be examined. The excitation radiation is generated in the light source module. Various lasers (for example, glass lasers, argon, argon/krypton, solid state lasers, TiSa lasers, diodes) are used for this purpose. Furthermore, the selection of wavelengths and the adjustment of the intensity of the required excitation wavelength is carried out in the light source module, i.e., using an acousto-optic crystal. The laser radiation subsequently reaches the scan module via a fiber or a suitable mirror arrangement.

The laser radiation, generated in the light source, is focused in the preparation in a diffraction-limited manner by means of the objective via the scanners, scanning optics and tube lens. The scanner is moved over the specimen point-by-point in x-y direction. The pixel dwell times when scanning over the specimen are mostly in the range of less than one microsecond to several seconds.

In confocal detection (descanned detection) of the fluorescent light, the light, which is emitted from the focal plane (specimen) and from the planes located above and below the latter, reaches a dichroic beam splitter (MDB) via the scanners. This dichroic beam splitter separates the fluorescent light from the excitation light. The fluorescent light is subsequently focused on a diaphragm (confocal diaphragm/pinhole), which is located precisely in a plane conjugate to the focal plane. In this way, fluorescent light components outside of the focus area are suppressed. The optical resolution of the microscope can be adjusted by varying the size of the diaphragm. Another dichroic blocking filter (EF), which again suppresses the excitation radiation, is located behind the diaphragm. After passing the blocking filter, the fluorescent light is measured by means of a point detector (PMT).

When using multiphoton absorption, the excitation of the dye fluorescence is carried out in a small volume, at which the excitation intensity is particularly high. This area is only negligibly larger than the detected area when using a confocal arrangement. Hence, there is no need to use a confocal diaphragm; and the detection can be carried out directly after the objective (non-descanned detection).

In another arrangement for detecting a dye fluorescence excited by multiphoton absorption, descanned detection is carried out again, but this time the pupil of the objective is imaged in the detection unit (non-confocal descanned detection).

From a three dimensionally illuminated image, only the plane (optical section), which is located in the focal plane of the objective, is reproduced by the two detection arrangements in connection with the corresponding single photon absorption or multiphoton absorption. By recording a plurality of optical sections in the x-y plane at different depths z of the specimen, a three dimensional image of the specimen can be generated then in a computer-assisted manner.

Therefore, the LSM is suitable for examining thick preparations. The excitation wavelengths are determined by the utilized dye with its specific absorption characteristics. Dichroic filters, adapted to the emission characteristics of the dye, ensure that only the fluorescent light, emitted by the respective dye, will be measured by the point detector.

Currently in biomedical applications a number of different cell regions are labeled simultaneously with different dyes (multi-fluorescence). In the prior art the individual dyes can be detected separately based on either different absorption characteristics or emission characteristics (spectra).

For separate detection, an additional splitting of the fluorescent light of a plurality of dyes is carried out with the secondary beam splitters (DBS); and a separate detection of the individual dye emissions is carried out in various point detectors (PMT 1-4).

Flow cytometers are used for examining and classifying cells and other particles. For this purpose the cells are dissolved in a liquid and are pumped through a capillary. In order to examine the cells, a laser beam is focused in the capillary from the side. The cells are dyed with different dyes or fluorescing biomolecules. The excited fluorescent light and the backscattered excitation light are measured. The fluorescence signal of the specimen is separated from the excitation light by means of dichroic beam splitters (MDB, see FIG. 1).

The size of the cells can be determined from the backscattered signal. Different cells can be separated/sorted or counted separately by means of the spectral characteristics of the fluorescence of individual cells. The sorting of the cells is carried out with an electrostatic field in different capillaries. The results, that is, for example, the quantity of cells with dye A in comparison to cells with dye B, are often displayed in histograms. The flow rate is typically about 10 to 100 cm/s. Therefore, a highly sensitive detection is necessary. According to the prior art, a confocal detection is carried out in order to limit the detection volume.

According to the prior art, so-called line scanners are also used, instead of point scanners (literature: Corle, Kino. *Confocal Scanning Optical Microscopy and Related Imaging Systems*. Academic Press, 1996). The basic construction corresponds in essence to that of an LSM, according to FIG. 1. However, instead of a point focus, a line is imaged in the specimen (3); and the specimen to be examined is scanned in only one direction (x or y). The image acquisition rate can be significantly increased by scanning a line, instead of a point. Therefore, this scanning method can be used for observing high speed processes in real time (real time microscopy).

In another arrangement for real time microscopy, according to the prior art, the entire field to be examined is illuminated by an expanded light source. However, only special point patterns of the total field to be scanned are uncovered by a rapidly rotating disk. These methods are usually referred to in the literature as the Nipkow disk methods (literature: Corle, Kino. *Confocal Scanning Optical Microscopy and Related Imaging Systems*. Academic Press, 1996).

Arrangements for screening dyes, such as in so-called chip readers, are similar in their optical construction to a laser scanning microscope. However, they scan a significantly larger image field for examining macroscopic specimens, for example, screening of active ingredients on a biochip. The edge length of the scan fields amounts to several 10 nm. These scan fields can be achieved, e.g. by increasing the scan angles of the galvo-scanners, by arranging the specimen in an intermediate image of the microscope arrangement or by a special objective arrangement (macro-objective), which images the intermediate image on the specimen in a magnified manner.

According to the prior art, the separation of the excitation light from the light emitted by the specimen is carried out by spectral separation using the Stokes shift by restricting the numerical aperture of the optics, used for specimen illumination and detection, or by splitting into different polarization directions.

Special dichroic beam splitters are used for the spectral separation of the excitation light from the light emitted by the specimen. As shown in FIG. 2A, these dichroic beam splitters are usually constructed in such a way that they reflect the excitation light as efficiently as possible and transmit the light emitted by the specimen as efficiently as possible. The reflection factor (reflectivity) is shown as a function of the wavelength. When using polarized excitation light, the minimum spectral bandwidth (s) of the reflected wavelength range is about 10 nm; the edge steepness (f) is usually greater than 5 nm. Therefore, according to the prior art, the light emitted by the specimen can be efficiently separated with a dichroic beam splitter when using an excitation wavelength. However, the efficiency decreases when a plurality of dyes with a plurality of wavelengths are excited simultaneously (multi-fluorescence microscopy), since a spectral overlapping of the excitation light and the emitted light usually occurs. Furthermore, a special beam splitter must be created each time when using different dyes with different absorption characteristics. In a wide field microscope, there is usually a broadband excitation of the specimen with light from a white light source with partial spectral overlapping of the excitation radiation and emitted radiation. Hence, the use of dichroic beam splitters, according to the prior art, results in poor efficiency of the separation of the excitation light from the emitted light.

The separation of excitation light from emitted light by restricting the numerical aperture of the specimen illumination optics (4 in FIG. 2B) can be carried out, for example, by illuminating the specimen with a restricted aperture, so that only the near-axis beams (1) arrive in the direction of the specimen (2). Since the emission is carried out in all spatial directions, this light from the specimen (2) can be collected in the rest of the aperture area. The separation of the excitation light from the emitted light is carried out subsequently by a partially fully reflecting (black area) plane plate (3). The detection of the light emitted by the specimen is carried out in the beam direction (5). The drawback with the methods for dividing the numerical aperture, known from the prior art (e.g. EP 1353209), is that, on the one hand, the efficiency of detection and, on the other hand, the optical resolution of the arrangement is impaired due to the restriction of the aperture. These two parameters are connected in this regard. For example, in order to achieve a highly efficient separation, the optical resolution decreases.

The drawback with all of the above described methods, according to the prior art, is that the separation of the excitation light from the light emitted by the specimen is carried out in a wavelength-dependent manner, i.e. not flexibly adjustable, or with a limited efficiency of typically 70% to 90%, depending on the required spectral characteristics and the quantity of illumination lines.

U.S. Pat. No. 6,510,001, U.S. Pat. No. 6,654,165, U.S. Published Patent Application No. 2003/0133189 and German Patent DE 19936573 disclose optical devices, where a spectrally flexible separation of the detection light from the excitation light can be carried out in an adjustable manner without any movement of mechanical components (FIG. 3). In this arrangement the MDB is replaced by an acousto-optic modulator AOTF (17, 4). It transmits the observation light (5, 12), coming from the direction of the specimen, so that it arrives in the direction of the detector (15). The excitation light (3, 9) runs at an angle relative to (12) and is diffracted into the joint specimen beam path (5) by means of the AOTF. Therefore, the frequency of the AOTF must be adjusted in such a manner that the excitation beam path and the detection beam path run colinearly. If this is not guaranteed, then the result is a reduction in the detection efficiency, particularly in the case of a confocal detection, and/or aliasing errors, because when different wavelengths are used, the excitation spots are not stacked. Special compensation devices are described in U.S. Pat. No. 6,967,764 B2. The drawback with these arrangements lies in the need for a plurality of tunable optical components that have a negative impact on the overall transmission.

U.S. Pat. No. 6,947,127 B2 discloses a method and optical devices, with which an achromatic separation of the detection light from the excitation light can be carried out in a wide field or in a line-scanning microscope. In this case the light radiation, which is excited in a specimen and/or which is backscattered and/or reflected by the specimen, is separated by focusing the specimen illumination in and/or in the vicinity of a pupil plane of the beam path between the specimen plane and the acquisition plane, and by providing means for a spatial separation of the illumination light from the detection light in this plane.

U.S. Published Patent Application No. 20040159797 A1 (FIG. 4) discloses a method and arrangement for changing the spectral composition and/or the intensity of the illumination light and/or the specimen light in an adjustable manner. Therefore, a spatial separation into radiation components of different polarization is carried out with the first polarization means (P1, P3); a spectral, spatial splitting of at least one radiation component is carried out with the first dispersion means (D1); the spectrally spatially split components are imaged (L1) on an element S; the polarization state of at least one part of the spectrally spatially split radiation component is changed by the action of the element S; and a spatial separation and/or combination of radiation components of different polarization are/is carried out by the second imaging means (L2) and the polarization means (P2, P4). In this respect a spatial combination of radiation components, which are changed and not changed with respect to their polarization state, is advantageously carried out by the second dispersion means (D2). The drawback with this arrangement lies in the number of optical components for a spectral spatial splitting, by means of which the efficiency of the arrangement is reduced. Furthermore, the manipulation of the polarization state of the spectral components at the element S is carried out with a linear array. Depending on the specified spectral resolution, this array is costly with regard to the electronic wiring. In addition, the speed is restricted when using a spatial light modulator and amounts to a few 10 ms.

In the prior art U.S. Published Patent Application No. 2004159797 A1 (FIG. 4), dispersive elements (e.g. prisms or gratings) D1 and D2, which split the light radiation spatially and spectrally along the Y coordinate and combine it again, are disposed between 2 bean splitter cubes each (P2 and P1 or P4 and P3). The optics L1 and L2 are positioned at a distance from their respective focal length f, which can also vary for the optics, between the dispersive elements D1 or D2 and an element for rotating the polarization, for example a spatial light modulator (SLM) S. The optics L1 and L2 together with the dispersive elements D1 and D2 are used to produce a spectral Fourier plane at the location of the SLM S. In this plane the spectral components of the light, coming from the direction 2 or the direction 1, are separated spatially along the Y coordinate. The SLM (e.g. SLM640 of the company Jenoptik, Germany) comprises a number of strips (in the case of the SLM 640 there are 640 strips), which can be actively controlled individually.

Depending on the active control of the respective pixel, the polarization direction of the light passing through can be varied. The SLM's, according to the prior art, are used in so-called pulse shapers (literature: Stobrawa et al. *Applied Physics* B72. pp. 627-630 (2002)). Therefore, the action of the SLM in combination with the dispersive elements results in a phase delay and/or a change in the amplitude of the spectral components of the light source. In addition, in contrast to the arrangements described below, the light source must be polarized linearly, because otherwise an energy loss occurs. Instead of an SLM, a plurality of adjustable lambda half-wave plates, which are arranged in the Fourier plane, can also be used, for example.

BRIEF SUMMARY OF THE INVENTION

The invention discloses a method and arrangements, by which the excitation light can be separated from the light radiation (e.g. fluorescence or luminescence), which is excited and/or backscattered in the specimen, in an especially advantageous manner with high efficiency. At the same time the number of optical components in the beam path is reduced, as compared to U.S. Published Patent Application No. 20040159797 A1, so that the result is a higher efficiency of the optical arrangement. Furthermore, the separation can be adjusted in a spectrally flexible manner without any movement of mechanical components and is, therefore, particularly suitable especially for use in multi-fluorescence microscopy, i.e. for simultaneous excitation of different dyes. Unlike the arrangements for separating the excitation beam path from the detection beam path according to the prior art, the optical resolution is not impaired by the arrangements, according to the invention. In addition, the suppression of the stray light is improved by at least one order of magnitude. Accordingly, fast switching between several excitation wavelengths or spectral detection wavelength ranges—so-called multi-tracking, as described in U.S. Pat. No. 6,462,345 B1,—can be realized in an especially simple manner.

Furthermore, it is possible to separate the light, scattered by the specimen in the direction of the detector, from the light, reflected on a direct path, and to measure it separately. In addition, a measurement of the polarization direction of the light, coming from the specimen, can be carried out.

Another advantage is that laser power fluctuations, caused by an unstable coupling into a glass fiber, can be prevented by automatic control, so that the output can be held constant at the site of the specimen.

Furthermore, the illumination distribution can be manipulated at the site of specimen interaction. This makes it possible to scan so-called regions of interest (ROI) in real time. In addition, the illumination methods known from wide field microscopy, such as oblique illumination, can be realized.

Furthermore, there is no need for the AOTF for selecting and fast switching the excitation wavelengths (FIG. 1, attenuator).

The solution, according to the invention, can be used in image generating microscope systems as well as in analytic microscope systems. The microscope systems are image generating systems, such as laser scanning microscopes for three dimensional examination of biological preparations with an optical resolution of up to 200 nm, near field scanning microscopes for high resolution examination of surfaces with a resolution of up to 10 nm, fluorescence correlation microscopes for quantitative determination of molecular concentrations and for measuring molecular diffusions. Also included are methods based on fluorescence detection for screening dyes and methods for flow cytometry.

In all of the aforesaid systems fluorescence dyes are used for specific labeling of the preparations. The aforesaid problem is solved by methods and arrangements, which are disclosed in the independent patent claims. Preferred further developments are disclosed in the dependent claims.

The quantity of the dye signatures, which may be used simultaneously, i.e., the quantity of the characteristics, for example, of cells that can be examined simultaneously, can be increased by means of the methods, according to the invention. When the spectral signatures of the individual dyes overlap extensively or are very close to one another, the detected wavelength range or numerical aperture must be limited, according to the prior art, for separate detection of the fluorescence signals of individual dyes. This reduces the sensitivity of detection, i.e., increases the noise of the detectors, because greater amplification must be used. This is avoided by the methods and arrangements of the invention.

BRIEF DESCRIPTION OF THE SEVERAL VIEWS OF THE DRAWINGS

FIG. 2A is a graph in which the reflection factor (reflectivity) of a dichroic beam splitter of a prior art LSM is shown as a function of the wavelength.

FIGS. 2B and 2C show the separation of excitation light from emitted light in the specimen illumination optics of a prior art LSM.

FIG. 4 is a schematic diagram of a prior art arrangement for changing the spectral composition and/or the intensity of the illumination light and/or the specimen light in an adjustable manner.

FIG. 5A is a schematic diagram of AOTF light components.

FIG. 5B is a schematic diagram of a colinear AOTF forming part of the subject invention.

FIG. 6A is a schematic diagram which shows the effect of the subject invention in the excitation beam path.

FIG. 6B is a schematic diagram which shows the effect of the subject invention in the detection beam path.

FIGS. 8A and 8B illustrate in schematic form another embodiment of a dichroic beam splitter (MDB) used in the present invention.

FIGS. 9A, 9B and 9C schematically illustrate yet another embodiment of a dichroic beam splitter (MDB) used in the present invention.

DETAILED DESCRIPTION OF THE INVENTION

Figure 1:
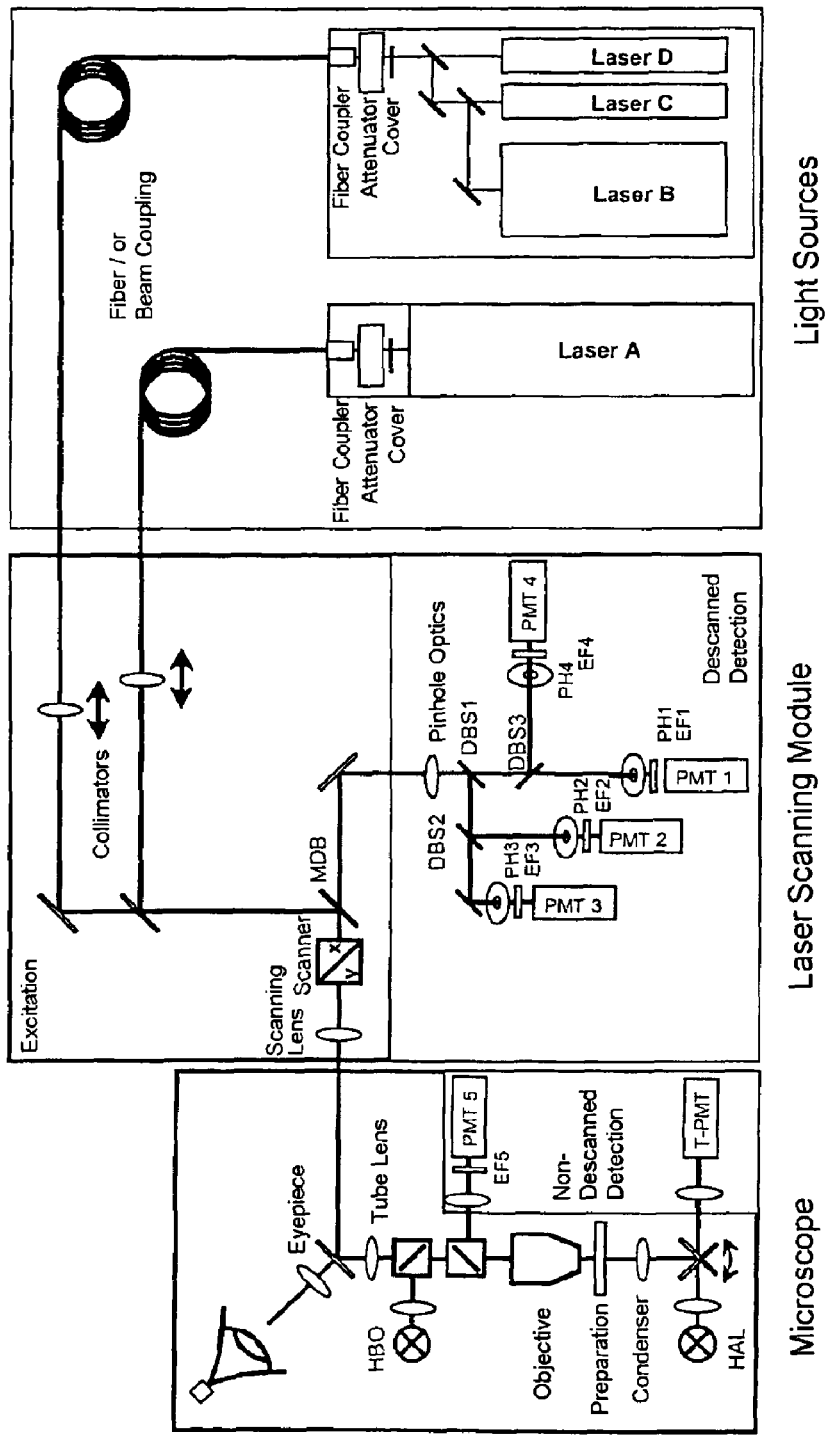
FIG. 1 is a schematic diagram of a confocal laser scanning microscope (LSM).
Figure 3:
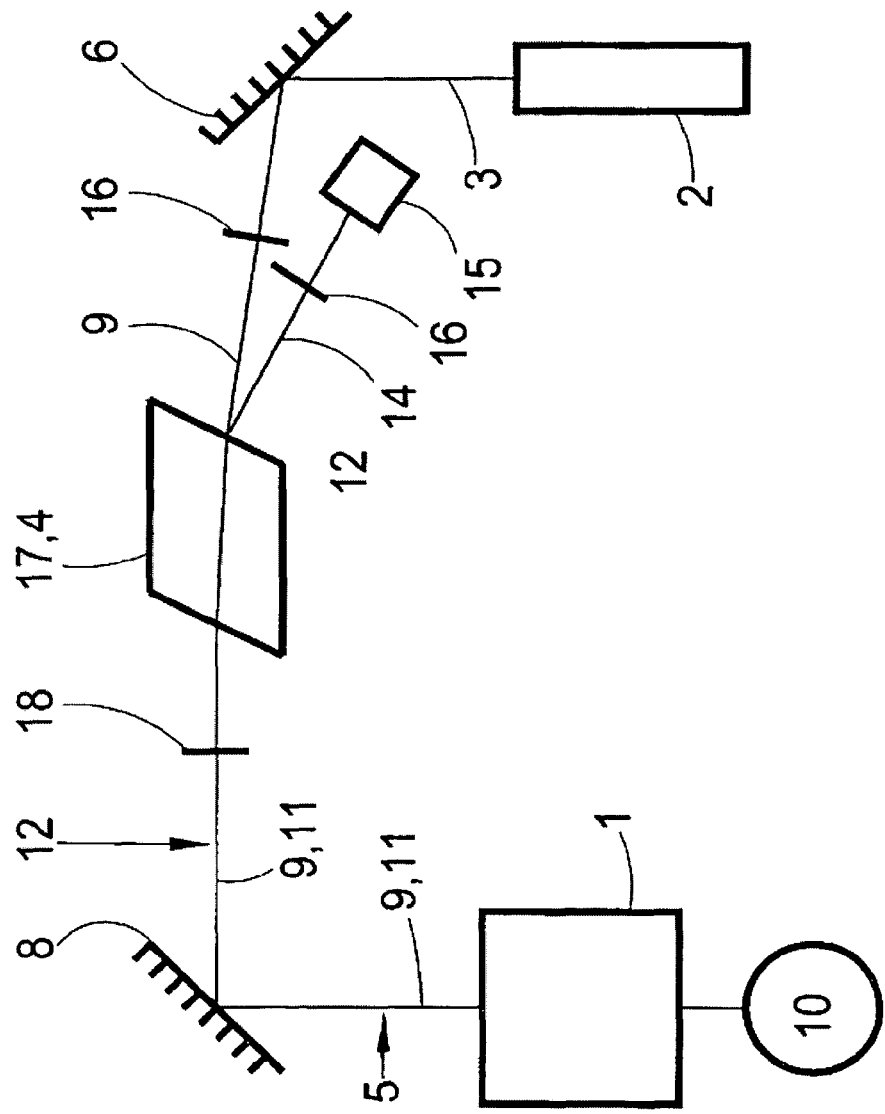
FIG. 3 shows the separation of detected light from excitation light carried out in an adjustable manner.

A plurality of arrangements, with which the light radiation (hereinafter the detection light), which is excited in a specimen and/or which is backscattered by the specimen, can be separated especially efficiently from the excitation light. Thus, the arrangements are especially suitable for fast multi-tracking with a spectrally adjusted, flexible separation of the excitation radiation from the detection light. In the following context, light radiation emitted by the specimen is light that is radiated from the specimen preferably in a large solid angle. This light radiation is usually not polarized (unpolarized) and/or the magnitude of the polarization differs from the polarization of the excitation light. They are in particular fluorescent light, luminescent light and backscattered light that are excited in the specimen.

1. Functional Principle of the Arrangement for Separating the Excitation Light from the Detection Light in a Variable Manner FIGS. 6A and 6B depict an arrangement for separating the excitation light from the detection light in a variable manner. The partial image A) shows the effect of the arrangement in the excitation beam path; partial image B), in the detection beam path. FIG. 6B shows in schematic form the construction of the arrangement for separating the excitation light from the detection light for the detection beam path; and FIG. 6A, for the excitation beam path. The arrangement comprises in essence at least three polarizing beam splitter cubes P1 to P3. P4 can be another polarizing beam splitter cube or a mirror. Examples of beam splitter cubes are Glan laser polarizing beam splitters, birefringent materials or especially microstructured beam splitters (e.g., MicroWires from the company Moxtek, Inc.; Orem, Utah, USA). An acousto-optic element is located between the polarizing beam splitter cubes.

The functional principle of the detection beam path is explained below with reference to FIG. 6B. Specimen light LD, which is coupled in at the coupling port KP2 in the direction of the arrow, (2) is separated into two orthogonally reflected polarization components Pol1 (circles in the drawing, pole direction in the observation direction) and continuous polarization components Pol2 (arrows in the drawing, pole direction in the direction of the arrow) at the pole splitter P2. The gray (I) and the black (II) symbols are supposed to represent lights of different wavelengths (e.g. black (II) fluorescence ($\lambda 2$) and gray (I) scattered excitation light ($\lambda 1$)). Pol1 of different wavelengths ($\lambda 1, \lambda 2$) arrives from P2 via P4; and Pol2 arrives from P2 directly at a number of regions of an acousto-optic tunable filter (AOTF) S; and in particular Pol1 arrives at region b; and Pol2, at region a. The AOTF rotates, for example, the polarization for the light radiation having wavelength $\lambda 2$ (shaded black (II)) by, for example, exactly 90 deg. (FIG. 4). Then the light reaches the pole splitters P1 and P3, where the gray (I) and the black (II) components (i.e. in this example the fluorescence radiation and the excitation radiation) are polarized orthogonally in both arms P2-P1 or P4-P2 (FIG. 4). Therefore, the excitation light (gray (I) components) exits through the coupling ports KP1 and KP5. Both polarization directions of the fluorescent light (black (II) components) exit jointly through the coupling port KP4.

The functional principle of the excitation beam path is derived accordingly and is explained with reference to FIG. 6A. Excitation light, which passes (arrow) through the inlet KP1, is separated into orthogonal polarization components Pol1 and Pol2, in KP2 at P1. The gray (I) and the black (II) symbols are supposed to represent in turn light of different wavelengths (e.g., black excitation light of wavelength $\lambda 2$ and red excitation light of wavelength $\lambda 1$). Pol2 arrives directly at the outlet KP6. Pol1 of different wavelengths ($\lambda 1, \lambda 2$) arrives from P1 at the AOTF S. The AOTF rotates, for example, the polarization for the light radiation $\lambda 2$ falling (shaded black II) by, for example, exactly 90 deg. For the wavelength $\lambda 1$ the AOTF rotates the polarization by an angle that is, for example, not equal to 90 deg. (preferably in the range from 0 deg. to 180 deg.). Then the light reaches P2. P2 separates the components, as a function of the polarization, into the outlet KP3 or into the outlet KP2. In the aforesaid example, the polarization for the wavelength λ2 was rotated by exactly 90 deg. by the AOTF. Therefore, all light of this wavelength is passed through P2 into the outlet KP3. In contrast, the polarization for the wavelength λ1 was rotated only by an angle not equal to 90 deg. Therefore, the light power is split into the two outlets KP2 and KP3. The division ratio is derived from the adjusted rotation angle of the polarization at the AOTF. A rotation of the polarization by an angle not equal to 90 deg. in the excitation beam path is suitable for attenuating the excitation light, because the ratio of the output in the coupling ports KP2 and KP3 can be set continuously according to the equation: P2/P3=tan (angle of rotation).

Therefore, owing to its varying spectral composition, the light radiation, which enters through the inlet KP1, can be spatially separated and adjusted in the various outlets KP2, KP3 and KP6, independently of the magnitude of the polarization, and can, therefore, be further processed optically and separately. At the same time owing to its varying spectral composition, the light radiation, which enters through the inlet KP2, can be spatially separated into the various outlets KP1, KP5 and KP4, independently of the magnitude of the polarization, and can, therefore, be further processed separately and optically. Therefore, the arrangement is suitable as the main color portions for separating the excitation beam path from the detection beam path.

It is possible to rotate the polarization by an angle that is not equal to 90 deg. in the detection beam path for the purpose of fluorescence measurement, but less expedient, because then the components of the fluorescent light also reach the coupling ports KP1 and KP5 and, thus, are not detected with a detector.

Birefringent media with a specified or flexible polarization rotation can be used as the polarization-rotating elements. Elements with flexible adjustment options are acousto-optic elements, like an AOTF, or electro-optical elements, like a Pockel cell. Elements with specified polarization rotation are, for example, delay plates, like lambda/4 plates.

Figure 13:
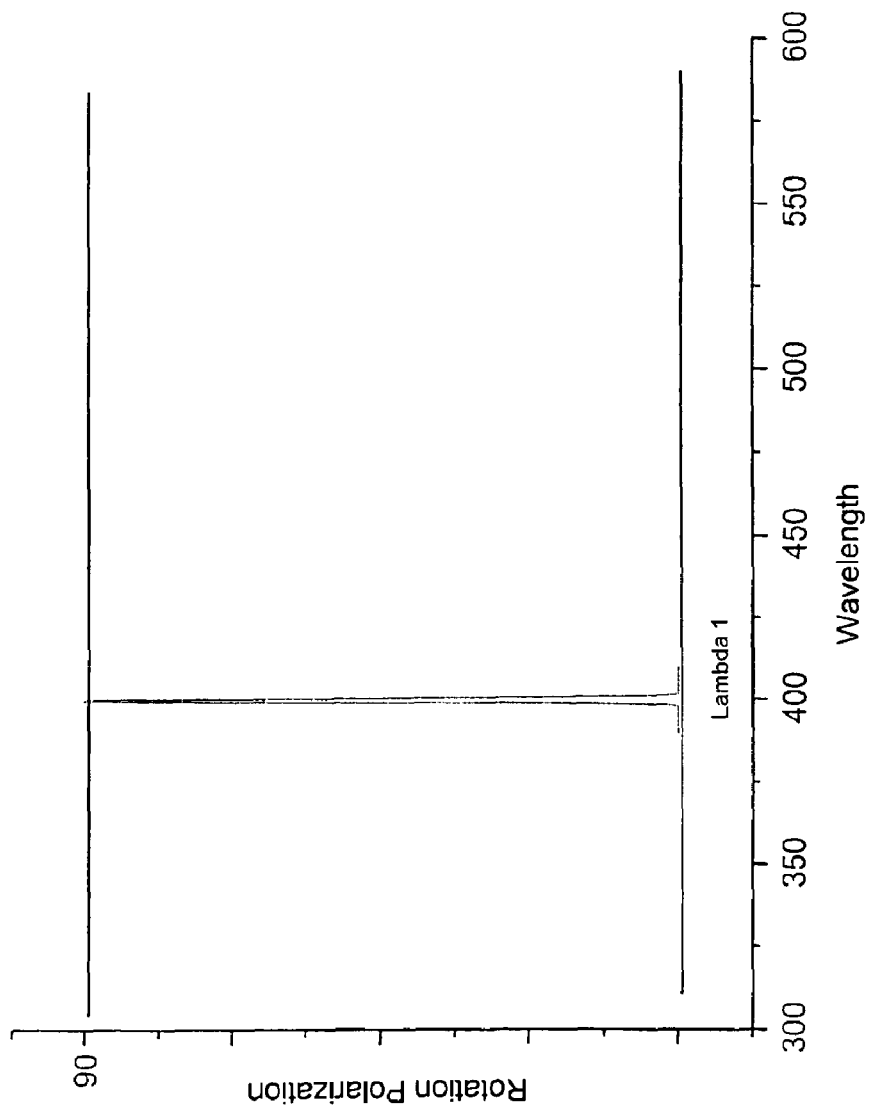
FIG. 13 is a graph showing the effect of an AOTF with an acoustic wave at frequency f1 and amplitude A1.

AOTFs with colinear acoustic and optic waves are especially suitable as the AOTF S. In contrast to non-colinear AOTFs, they can rotate the polarization without affecting the direction of the optic wave. In the case of a non-colinear AOTF (FIG. 5A) the acoustic wave (between couplers 3 and 4) is angled relative to the incident radiation (1). After the AOTF light components (2a), diffracted at the acoustic wave, and undiffracted light components (2b) occur. In the colinear AOTF (FIG. 5B), used according to the invention, an acoustic wave of a determined frequency is applied between the couplers (transducers 3, 4) for rotating the polarization of a specific wavelength. The amplitude of the acoustic wave determines the magnitude of the polarization rotation of the optic wave at the outlet 2. By overlapping acoustic waves of different frequency and amplitude, the polarization states of different wavelengths can be varied simultaneously, so that several wavelength ranges can be optically switched simultaneously. For more details with respect to how colinear AOTFs function, reference is made to the literature: *Design and Fabrication of Acousto-Optic Devices*, ed. Goutzoulis, Pape, Dekker Inc. 1994, USA. FIG. 13 shows the effect of the AOTF with an acoustic wave at frequency f1 and amplitude A1, which causes, for example, a 90 deg. rotation of the polarization of the input light at wavelength lambda1. The polarization direction of the light at other wavelengths is not changed.

Figure 7:
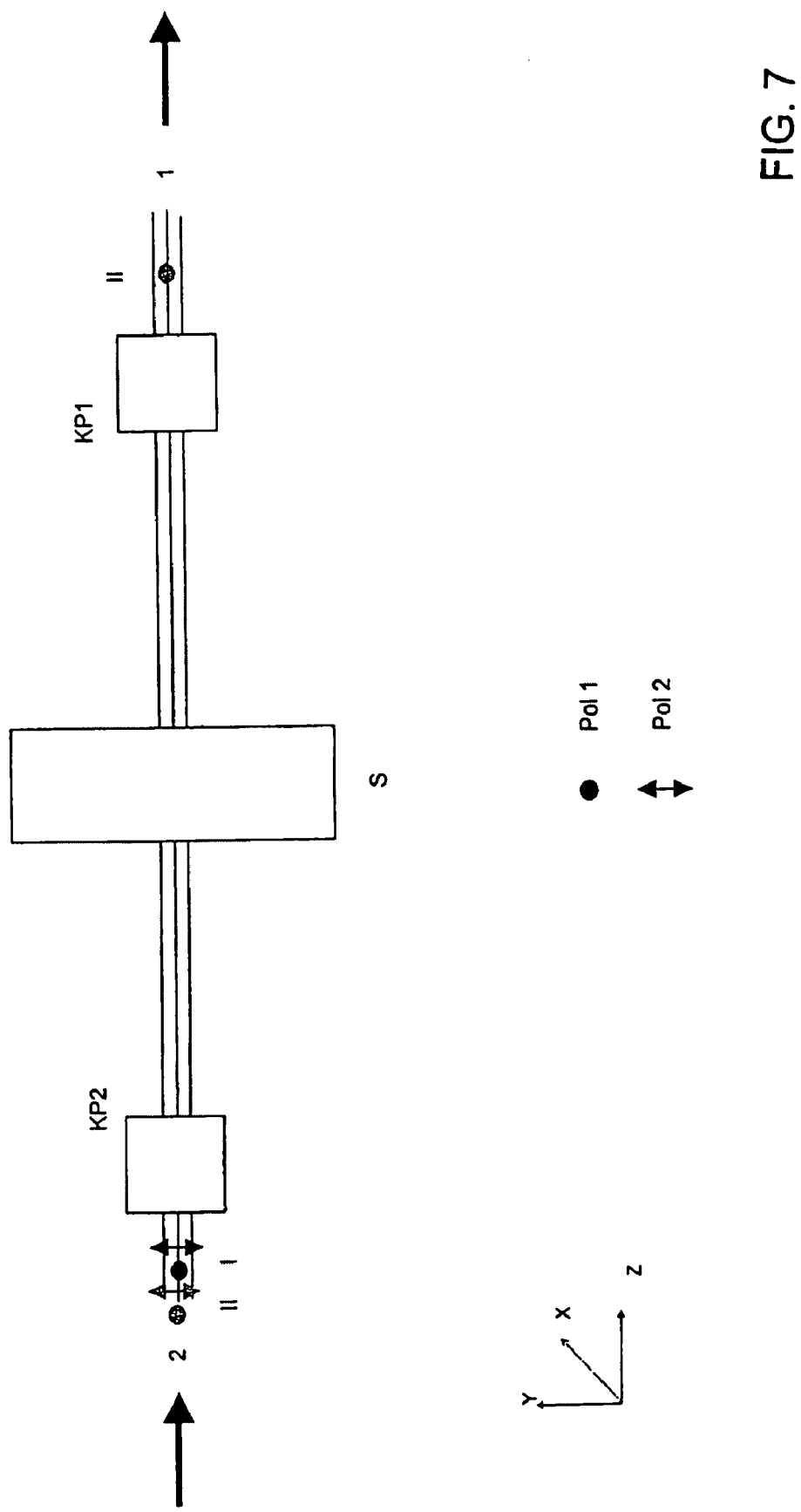
FIG. 7 is a schematic diagram of the arrangement of FIGS. 6A and 6B in the Y-Z plane.

FIG. 7 shows the arrangement from FIG. 6 in the Y-Z plane. Due to the optical elements preferably no deflection of the excitation light and/or the detection light is carried out.

FIG. 8 shows another advantageous design of the MDB, wherein birefringent media M1, M2 are used as the polarization splitters. They can be birefringent crystals, like calcite. The function and the description of the ports is analogous to that of FIG. 6. Only the polarization splitters are replaced with birefringent media.

This has the advantage that the polarization splitting can be carried out over large spectral bandwidths with high efficiency. Furthermore, the ranges a. and b. can be arranged in an especially simple way so that they lie very close to one another.

The KPs are the above described coupling ports labeled with the respective reference numerals.

FIG. 9 shows another advantageous design of the MDB. In this case the number of optical components is minimized. The arrangement uses a single polarization-splitting element P. The light from port 2 (e.g. specimen) is split into its polarization components at P and arrives via a lens L at or in AOTF (S), where S is disposed in the focal point of the lens L. The light passes twice through AOTF S; and, thus, the AOTF S is operated in reflection. Therefore, the reflecting surface is arranged at a small angle. The reflecting surface can also be in an advantageous manner a surface of the AOTF crystal. By tilting S or the mirror at another angle, the light reaches the lens L; and beams, which run in the direction P, form parallel to the input beam. If the polarization at the AOTF S is not changed, then both beams arrive at P from the port 4 (e.g. detector). If, however, the polarization at the AOTF is changed, then the polarization components arrive in the direction of port 1 (e.g. light source). Since the parallel shift of both polarization components at the ports 1 and 4 is extremely small, both components at, for example, 4 can be guided to a joint detector. The parallel shift between ports 1 and 2 is chosen in such a manner that a spatial separation of the two beams is possible (e.g. by means of M1 in the figure).

2. Laser Scanning Microscope

Figure 10:
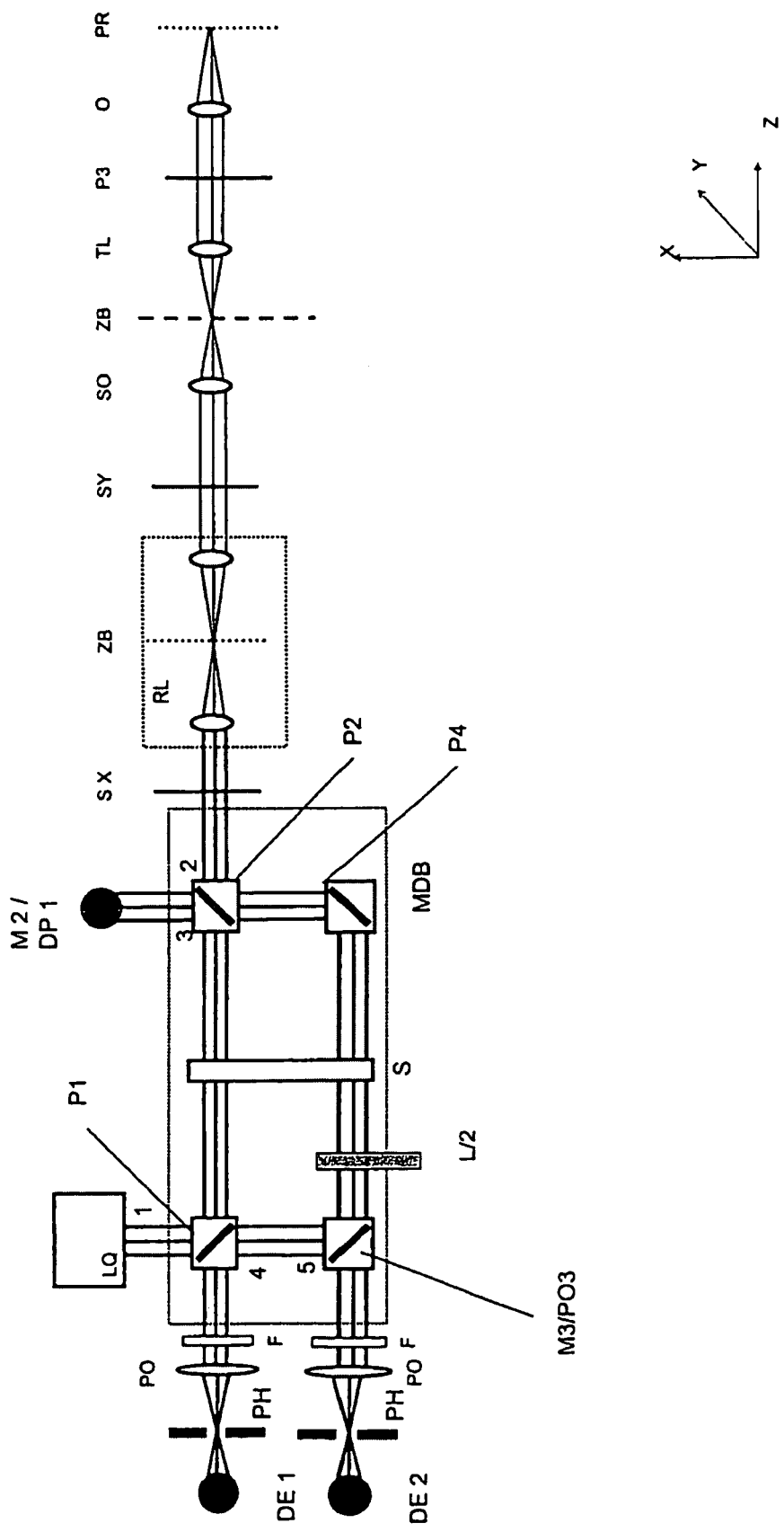
FIG. 10 is a schematic diagram illustrating the inventive arrangement for a laser scanning microscope (LSM) in the X-Z plane.

FIG. 10 shows in schematic form the inventive arrangement for a laser scanning microscope (LSM) in the X-Z plane. The functional principle, described under 1 (with reference to FIGS. 6 to 9), can be applied analogously to a microscope for separating fluorescence radiation from excitation radiation. In an LSM the specimen is illuminated with a point focus, which is moved by means of the scanners SX and SY in the XY plane. For this purpose the preferably linearly polarized light source LQ in the MDB is coupled in via the port 1 at P1. Then the light of the light source LQ arrives preferably at an area a of the AOTF S. If the excitation light is supposed to reach the specimen, then the AOTF is switched in such a manner that the polarization direction of the light is rotated by 90 deg.; and the excitation light reaches the outlet 2 of the MDB.

If a corresponding acoustic wave with adapted frequency and amplitude is applied to the AOTF, then the polarization direction of the excitation light is rotated by an angle that is not equal to 90 deg. Therefore, depending on the polarization direction, a part of the light reaches the outlet 2; and the rest of the component reaches the outlet 3. At outlet 3 there is a monitor diode M2 for determining the excitation light output, which, as the controlled variable, can be used to compensate for the intensity fluctuations, caused by coupling into a plurality of polarization direction of, for example, a glass fiber. Furthermore, this operating mode can also be used for fast switching or attenuating individual wavelengths of the light source.

The linearly polarized excitation light, coupled in the direction of the outlet 2, reaches the scanners SX and SY, which are located in pupil planes of the microscope arrangement that are conjugate to one another and the back focal plane of the objective P3, so that the scanners can move the excitation point, which is focused in a diffraction-limited manner, in the XY plane of the specimen—that is, scan the specimen. The imaging in the specimen is carried out by means of the scan optics SO, the tube lens TL and the objective O. The relay optics RL generate the conjugate pupil planes SX and XY of the microscope arrangement. In special arrangements, according to the prior art, the relay optics can also be dispensed with. For example, they can be omitted when the distance between SX and SY is decreased.

The light emitted by the specimen is collected by the optics O (e.g. a microscope objective) and imaged jointly with the tube lens TL in an intermediate plane ZB of the microscope unit. From there the light arrives in turn via the scanners SX/SY and the relay optics RL at the inlet 2 of the MDB. Since the light emitted by the specimen is usually unpolarized, it is separated into two orthogonal polarization directions Pol1 and Pol2 at the beam splitter P2. If, for example, fluorescent light is excited in the specimen, then because of the Stokes shift the spectrum of the light is spectrally shifted in comparison to the excitation light. Therefore, the AOTF S does not rotate the polarization in the areas a. and b. The element PO3 is constructed as a mirror. Therefore, the fluorescent light reaches the outlet 4. However, the backscattered unpolarized excitation light reaches outlet 5, because the polarization is rotated, according to the adjustment of the excitation light, by the acoustic wave in the AOTF S.

Then the light of the specimen, which reaches the outlet 4 of the MDB, is focused by means of imaging optics PO through a confocal diaphragm PH, so that the detection light, occurring outside of the focus, is suppressed. In the case of non-confocal detection, the diaphragm can be dispensed with. Behind the confocal diaphragm there is a detector DE1, which detects the light radiation excited in the specimen. When recording fluorescence or luminescence, an emission filter (dichroic filter) F can be swiveled in for additionally suppressing the excitation light backscattered by the specimen, or for limiting the spectral detection area.

If the polarization of the emitted light of the specimen is supposed to be detected (e.g. when determining fluorescence anisotropy), this can be carried out with two detectors. For this purpose PO3 is constructed as a polarizer; and another detector DE2 is disposed at the outlet 5. A lambda/2 plate L/2 is disposed between PO3 and S; the polarization is rotated by 90 deg. The respective polarization can be composed of two components, which are polarized orthogonally to one another. The two orthogonally polarized components are separated with DE1 and DE2. Then the respective polarization can be derived by forming the ratio of the signals of the detectors DE1 and DE2.

The backscattered or reflected excitation light of the specimen, which travels through the outlet 5 of the MDB, can also be focused through a confocal diaphragm (PH) by means of imaging optics (PO), thus suppressing the detection light occurring outside of the focus. Behind the confocal diaphragm there is a detector (DE2), which detects the excitation radiation, backscattered by the specimen. The emission filter F ceases to be applicable.

Figure 11:
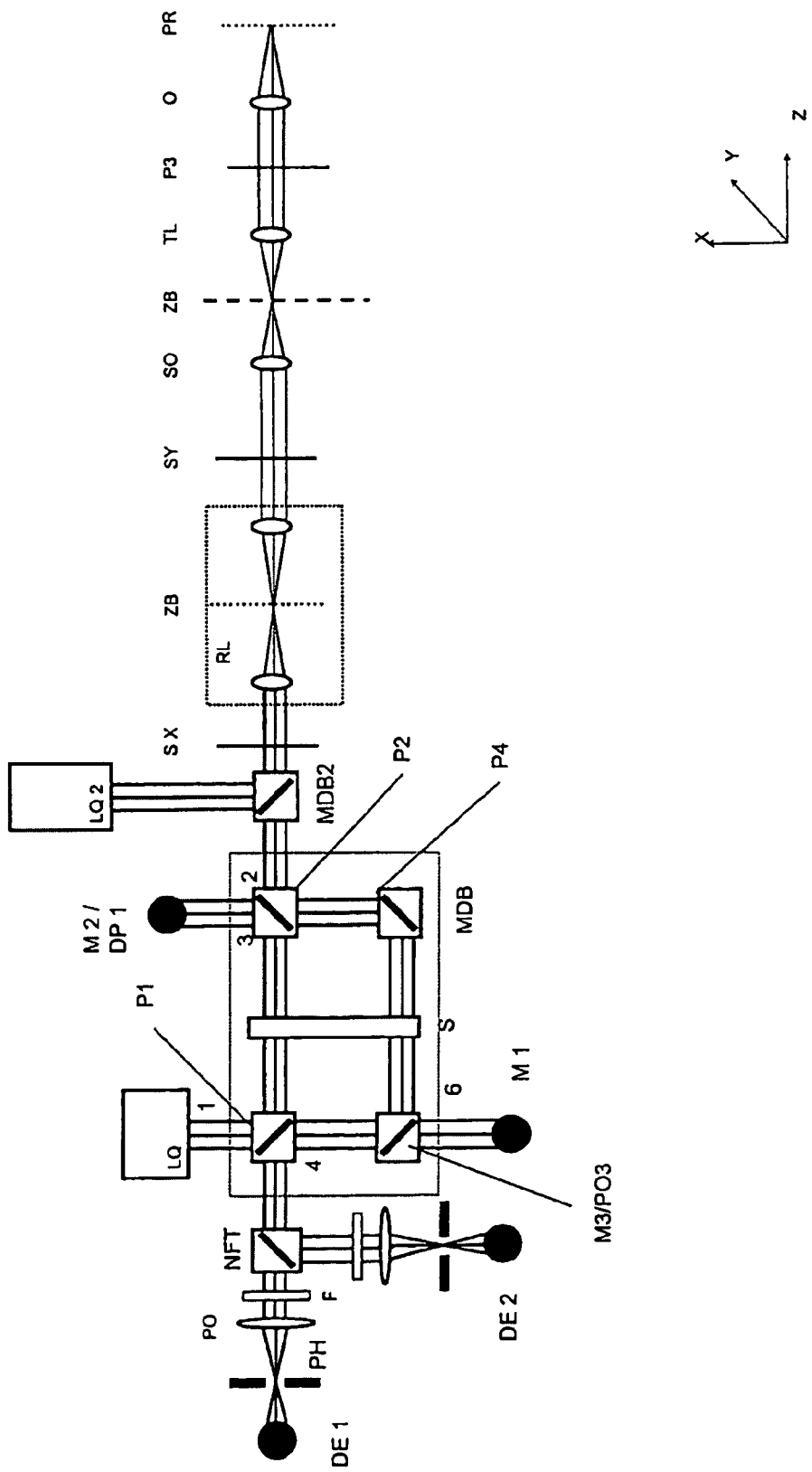
FIG. 11 is a schematic diagram illustrating another inventive arrangement for a laser scanning microscope (LSM) in the X-Z plane.

FIG. 11 shows in schematic form another design of the inventive arrangement for a laser scanning microscope LSM in the X-Z plane, in which another light source LQ2, which does not run through the MDB1, is coupled.

In addition to the arrangement, explained above with reference to FIG. 10, the outlet 6 exhibits another monitor diode M1. If the excitation radiation is coupled not only in one polarization direction Pol1, but also in the polarization direction Pol2, then M1 measures the coupled power. If the measurement signal M1 diverges from a desired value, then the AOTF S can be actuated correspondingly in such a manner that another commensurate desired value is set at M2. Owing to this adjustment, fluctuations in the coupling efficiency, e.g., in a glass fiber, which is located between the light source LQ and the input 1 of the MDB, can be compensated for. In the case of polarization-achieving glass fibers the coupling efficiency and, thus, the light power, coupled in the direction of the specimen, can be influenced by disadjusting the coupling into the glass fiber or by coupling into different polarization directions.

Currently in fluorescence microscopy a variety of light sources from a wide spectral range are used. Owing to the lower transmission of the AOTF in specific wavelength ranges, e.g. with UV light sources (less than 400 nm) or with multiphoton excitation (greater than 800 nm), the coupling of the light sources by the AOTF S may or may not be desired. These light sources LQ2 can be combined with a conventional beam splitter MDB 2 between the outlet 2 and the first scanner, e.g. SX, with the light sources LQ1, which travel through the AOTF S. In the case of these light sources the detection is usually carried out in the wavelength range between 400 and 800 nm, i.e., for example, through the AOTF S or with detectors, according to the prior art.

In addition, the light, which is emitted by the specimen and which impinges on the outlet 4 of the MDB 1, can be split, according to the prior art, with dichroic beam splitters NFT into different confocal detectors (e.g. DE1 and DE2).

In all of the inventive arrangements the outlets can be also be exchanged accordingly.

The MDB is also suitable for scanning regions of special interest ROI (see EP 977069 A2). See FIG. 10. In this case the laser light of specific wavelength and output is unblocked only for specific regions, which are selected beforehand by the user. The wavelength or the adjustment of the excitation output is switched over by means of actuating in a suitable manner the AOTF S, with the result that the polarization state is changed accordingly.

Figure 12:
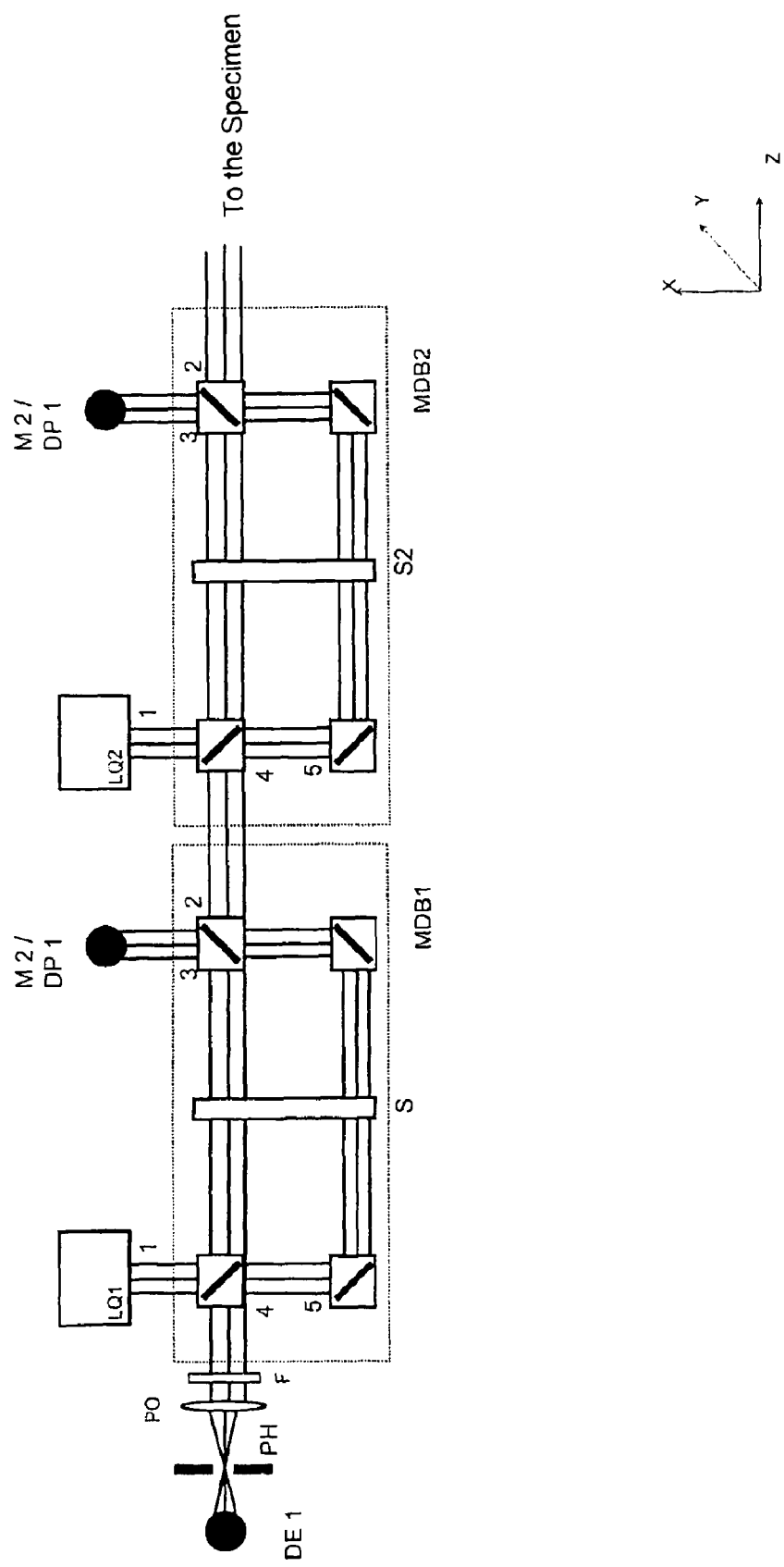
FIG. 12 is a schematic diagram of a series of MDBs arranged in succession.

In principle, several MDB arrangements of the invention can be arranged in succession. For this purpose, the outlet (2) of the first MDB is coupled into the inlet (1) of the second MDB (see simplified schematic FIG. 12). Therefore, two light source modules (LQ1 and LQ2) can be coupled, for example, in a joint specimen beam path.

In principle, the function of the illustrated scanners can also be replaced with a corresponding scan table (object scanner).

What is claimed is:

1. A microscope having a light source for illuminating a specimen, means for detecting light coming from the specimen, and a device for controlling light radiation coming from at least one of the light source and the specimen, the device comprising:
   a plurality of light outlets;
   first polarizing means for spatially separating the light radiation into components of different polarization;
   a collinear acousto-optic tunable filter downstream of the first polarizing means for affecting the polarization of the components in a wavelength-dependent manner, wherein the light radiation incident on the acousto-optic tunable filter is in a condition free of dispersion, and wherein the acousto-optic tunable filter passes the light radiation in a condition free of dispersion; and
   second polarizing means downstream of the acousto-optic tunable filter for combining the components of different polarization while spatially separating affected and unaffected wavelengths of the components to different light outlets.

2. The microscope as claimed in claim 1, wherein the first polarizing means are arranged for spatially separating the light radiation coming from the light source into illumination components of different polarization;

wherein the second polarizing means are arranged for combining the illumination components while spatially separating affected and unaffected wavelengths of the illumination components to the different light outlets and for spatially separating the light radiation coming from the specimen into detection components of different polarization; and wherein the first polarizing means are arranged for combining the detection components while spatially separating affected and unaffected wavelengths of the detection components to different light outlets.

3. The microscope as claimed in claim 1, wherein the acousto-optic tunable filter is constructed so that it does not spectrally split the light radiation passing therethrough.

4. The microscope as claimed in claim 1, wherein the light source is a laser and wherein the microscope further comprises means for laser-scanning the specimen.

5. The device, as claimed in claim 1, further comprising means for descanned detection of radiation light coming from the specimen.

6. The device, as claimed in claim 1, further comprising means for partial descanned detection in one direction of radiation light coming from the specimen.

7. The device, as claimed in claim 1, further comprising means for non-descanned detection of radiation light coming from the specimen.

8. The device, as claimed in claim 1, further comprising a line detector for spectrally resolved measurement.

9. The device, as claimed in claim 1, wherein the first polarizing means and the second polarizing means are provided by a single polarization-splitting element.

10. A microscope having a light source for illuminating a specimen, means for detecting light coming from the specimen, and a device for controlling light radiation coming from at least one of the light source and the specimen, the device comprising:

a plurality of light outlets;

first polarizing means for spatially separating the light radiation into components of different polarization;

a collinear acousto-optic tunable filter downstream of the first polarizing means for affecting the polarization of the components in a wavelength-dependent manner, and second polarizing means downstream of the acousto-optic tunable filter for combining the components of different polarization while spatially separating affected and unaffected wavelengths of the components to different light outlets, wherein between the first polarizing means and the second polarizing means, the device is free from dispersion means.

\* \* \* \* \*